United States Patent [19]

Wingen et al.

[11] Patent Number: 5,344,585
[45] Date of Patent: Sep. 6, 1994

[54] USE OF 4-FLUOROPYRIMIDINE DERIVATIVES AS COMPONENT FOR FERROELECTRIC LIQUID CRYSTAL MIXTURES

[75] Inventors: Rainer Wingen, Hattersheim am Main; Gerhard Illian, Frankfurt am Main, both of Fed. Rep. of Germany

[73] Assignee: Hoechst Aktiengesellschaft, Frankfurt am Main, Fed. Rep. of Germany

[21] Appl. No.: 758,633

[22] Filed: Sep. 12, 1991

[30] Foreign Application Priority Data

Sep. 14, 1990 [DE] Fed. Rep. of Germany ....... 4029165
Sep. 27, 1990 [DE] Fed. Rep. of Germany ....... 4030582

[51] Int. Cl.$^5$ .................... C09K 19/34; C07D 239/02; G02F 1/13
[52] U.S. Cl. .............................. 252/299.61; 544/298; 359/104
[58] Field of Search ..................... 252/299.61; 544/298

[56] References Cited

U.S. PATENT DOCUMENTS

| | | | |
|---|---|---|---|
| 4,704,227 | 11/1987 | Krause et al. | 252/299.61 |
| 4,808,333 | 2/1989 | Huynh-ba et al. | 252/299.66 |
| 4,886,622 | 12/1989 | Miyazawa et al. | 252/299.61 |
| 5,032,314 | 7/1991 | Ushioda et al. | 252/299.65 |

FOREIGN PATENT DOCUMENTS

| | | |
|---|---|---|
| 0154840 | 9/1985 | European Pat. Off. . |
| 269062 | 6/1988 | European Pat. Off. . |
| 0315455 | 5/1989 | European Pat. Off. . |
| 0158137 | 1/1990 | European Pat. Off. . |

OTHER PUBLICATIONS

German Abstract 85-257036/42, Merck Patent GmbH, New 4-methyl- on 4-fluoro-pyrimidine derivs.-contg. phenylene, cyclohexylene, dithian-diyl or bicyclo-octylene gps. and used as components of liq. crystalline phases for displays.

*Primary Examiner*—Robert L. Stoll
*Assistant Examiner*—C. Harris
*Attorney, Agent, or Firm*—Curtis, Morris & Safford

[57] ABSTRACT

The use of a fluoropyrimidine derivative of the general formula (I) as component in a ferroelectric liquid crystal mixture comprising 2 to 20 components,

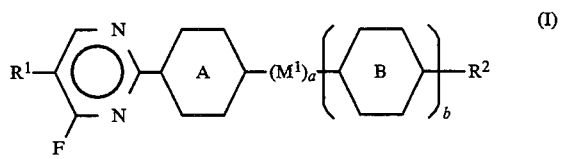

in which the symbols have the following meaning:
$R^1$ and $R^2$ independently of one another are, for example, straight-chain or branched alkyl having 1 to 16 carbon atoms,
a and b are, for example, both equal to 0 or 1,

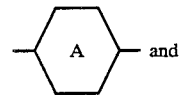

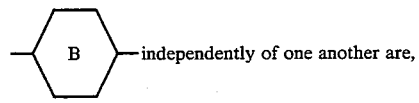

for example, phenylene or cyclohexylene, and —M$^1$— is, for example, —CO—O—, —O—CO—, —CH$_2$—O— or —O—CH$_2$, leads to improved switching characteristics in electrooptical display devices.

7 Claims, No Drawings

USE OF 4-FLUOROPYRIMIDINE DERIVATIVES AS COMPONENT FOR FERROELECTRIC LIQUID CRYSTAL MIXTURES

The unusual combination of anisotropic and fluid behavior of liquid crystals has led to their use in a multiplicity of different electrooptical switching and display devices. In these applications, the electrical, magnetic, elastic and/or thermal characteristics of the liquid crystals can be utilized for changes in orientation. Optical effects can be achieved, for example, with the aid of birefringence, the intercalation of dye molecules displaying dichroic absorbance ("guest-host mode") or light scattering.

In order to meet the continuously increasing demands in practice for the various fields of application, there is a continuing demand for novel, improved liquid crystal mixtures and thus also for a multiplicity of mesogenic compounds of diverse structure. This applies both in respect of the fields in which the nematic LC phases are used and in respect of those using smectic LC phases.

In recent years ferroelectric liquid crystal mixtures (FLC mixtures) have attracted particular interest (see, for example, Lagerall et al., "Ferroelectric Liquid Crystals for Display", SID Symposium, October Meeting 1985, San Diego, Ca. USA). For practical use of ferroelectric liquid crystals in electrooptical displays, chiral, tilted-smectic phases, such as, for example, $S_c^*$ phases are required [see R. B. Meyer, L. Liebért, L. Strzelecki and P. Keller, J. Physique 36, L-69 (1975)], which are stable over a wide temperature range. This aim can be achieved by means of compounds which themselves form such phases, for example $S_c^*$ phases, or by doping compounds which form non-chiral tilted-smectic phases with optically active compounds [see M. Brunet, Cl. Williams, Ann. Phys. 3, 237 (1978)].

Since the liquid crystal temperature range of the majority of ferroelectric liquid crystal systems is too small, there is a continuing demand for novel components and novel liquid crystal mixtures which form a $S_c$ phase in the region of room temperature.

In EP-B 0,158,137, 4-fluoropyrimidines are described as compounds and as mixing components in general. However, they have no or only a slight tendency to form smectic phases.

The present invention relates to the use of particular 4-fluoropyrimidine derivatives as component for a liquid crystal mixture, at least one 4-fluoropyrimidine of the general formula (I) being employed as component in a ferroelectric liquid crystal mixture comprising 2 to 20 and preferably 2 to 15 components.

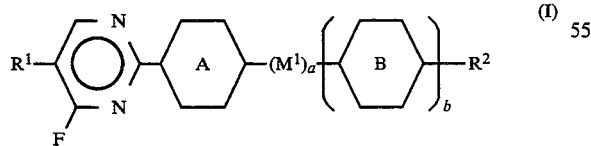
(I)

In this formula the symbols have the following meaning:

$R^1$ and $R^2$ independently of one another are straight-chain or branched alkyl having 1 to 16 carbon atoms, it being possible for one or two non-adjacent —CH$_2$— groups to be replaced by —O—, —S—, —CO—, —CO—O—, —O—CO—, —CH=CH—, —OC(O)O—, —C≡C—, or —Si(CH$_3$)$_2$—, or are one of the following groups:

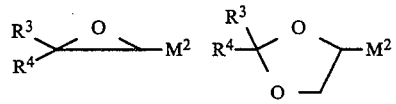

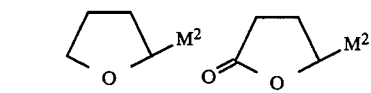

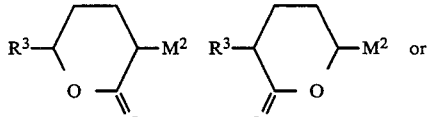

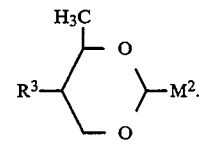

$R^3$ and $R^4$ independently of one another are H or alkyl having 1 to 16 carbon atoms or alkenyl having 2 to 16 carbon atoms, or $R^3$ and $R^4$ together are —(CH$_2$)$_4$ or —(CH$_2$)$_5$, —M$^1$— is —CO—O, —O—CO—, —CH$_2$—O—, —O—CH$_2$—, —C≡C—, —CH=CH—, —CH$_2$—CH$_2$—, —CH$_2$CH$_2$CH$_2$CH$_2$—, —CH$_2$CH$_2$C-H$_2$O—

—M$^2$— is —CH$_2$—O—,

a single bond, —O—CH$_2$—,

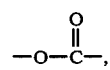

a and b independently of one another are zero or one, on condition that a is zero if b is zero, and

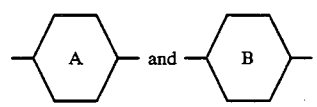

independently of one another are 1,4-phenylene, 1,4-cyclohexylene, 2,5-pyridinediyl or (1,3,4)thiadiazol-2,5-diyl.

In a preferred embodiment, the symbols in formula (I) have the following meaning:

$R^1$ and $R^2$ independently of one another are alkyl having 1 to 16 carbon atoms, it being possible for one —CH$_2$— group to be replaced by —O—, —CO—O—, —O—CO—,

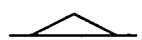

or —Si(CH$_3$)$_2$—, or are

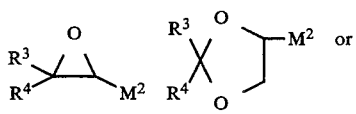

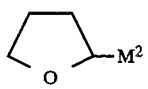

—M$^1$— is —CO—O, O—CO, CH$_2$—O or OCH$_2$
—M$^2$— is CO—O, CH$_2$O

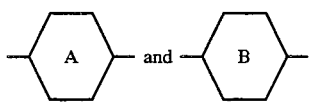

independently of one another are 1,4-phenylene or 1,4-cyclohexylene,
R$^3$ and R$^4$ are both H or C$_1$-C$_5$-alkyl, or R$^3$ and R$^4$ together are —(CH$_2$)$_5$—, and
a, b independently of one another are zero or one, on condition that a is zero if b is zero.

Particularly preferably, R$^1$ and R$^2$ independently of one another are alkyl having 5 to 12 carbon atoms, it being possible for one —CH$_2$— group to be replaced by —O— and for a further —CH$_2$— group, in particular the terminal —CH$_2$— group of the alkyl, to be replaced by

or are

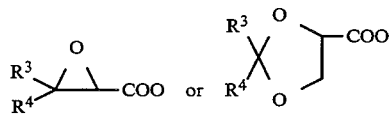

—M$^1$— is CO—O or O—CO,

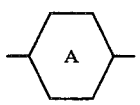

is 1,4-phenylene,

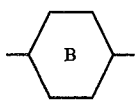

is 1,4-cyclohexylene and
R$^3$ and R$^4$ are both H or C$_1$-C$_5$-alkyl, or R$^3$ and R$^4$ together are —(CH$_2$)$_5$—, and
a=b and is zero or one.

The invention also relates to a ferroelectric liquid crystal mixture comprising 2 to 20 components, which mixture contains at least one 4-fluoropyrimidine of the general formula (I) as one component.

This FLC mixture in general contains 0.1 to 80, preferably 1 to 60 and in particular 1 to 20 mol-% of the compound of the formula (I). If several of the compounds are contained in the mixture, the total content is 0.1 to 80 mol-%, preferably 1 to 60 mol-%.

The other constituents of the mixtures are preferably selected from the known compounds having nematic, cholersteric and/or tilted-smectic phases; these compounds include, for example, thiadiazole, difluorophenyls, fluoropyridines, pyridines, biphenyls, terphenyls, phenylcyclohexanes, cyclohexylbiphenyls, pyrimidines, cinnamic acid esters, cholesterol esters or various bridged esters of p-alkylbenzoic acids.

The liquid crystal mixtures described can advantageously be used in electrooptical switching and display devices (FLC light valves or displays) and lead, for example, to a shortening in the switching time and to dissemination of the nematic phase. These devices have, inter alia, the following constituents: a liquid crystal mixture (containing a 4-fluoropyrimidine), outer plates (for example made of glass or plastic) coated with transparent electrodes (two electrodes), at least one alignment layer, spacers, sealing frames, polarizers and also, for color displays, thin color filter layers. Further possible components are antireflex, passivation, compensation and barrier layers and also electrically non-linear elements, such as, for example, thin film transistors (TFT) and metal-insulator-metal (MIM) elements. The general construction of liquid crystal displays has already been described in detail in relevant monographs (for example E. Kaneko, "Liquid Crystal Displays", KTK, Scientific Publishers, 1987, pages 12–30 and 163–172).

The 4-fluoropyrimidines of the formula (I) are chemically, photochemically and thermally stable; they preferably contain both S$_c$ phases and nematic phases. The 5-alkoxy-2-(4-alkoxy)phenyl-4-fluoropyrimidines, which in addition to the S$_c$ phase also have even lower melting points than their non-fluorinated analogs, are particularly preferred. Preferably, the fluorine substitution further suppresses the formation of more highly ordered phases.

The invention relates to a process for the preparation of 4-fluoropyrimidine derivatives, in particular those of the formula (I), in which process pyrimidin-4-one compounds of the formula (II) are reacted with an aminofluorosulfurane of the formula (III)

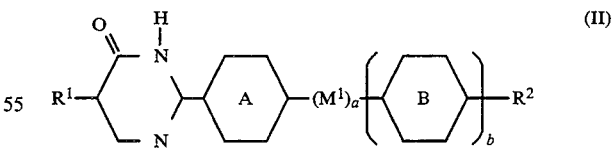

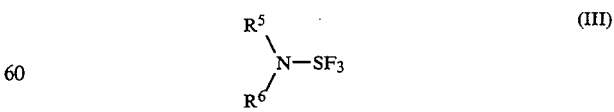

in which R$^5$ and R$^6$ independently of one another are C$_1$- to C$_{10}$-alkyl, or R$^5$ and R$^6$ together are (—CH$_2$)$_c$(—O)$_d$(—CH$_2$)$_e$, in which
c=an integer from 1 to 5,
d=zero or 1 and
e=an integer from 1 to 5.

In this process a pyrimidin-4-one compound (II)—the preparation is carried out analogously to Boller et al., Z. Naturf. 33b 433 (1978)—is reacted directly with a fluorinating reagent to give (I). Compared with the process in EP-B 0,158,137, comprising conversion of pyridimidin-4-one to the corresponding chlorinated compounds using $POCl_3$ and subsequently reaction of the latter with the fluorinating agent to give the fluorinated compounds, the process according to the invention has the advantage of avoiding the chlorination step—which is frequently associated with dark discolorations and the formation of impurities which are difficult to separate off. In principle, the fluorination process described is generally applicable to other pyrimidin-4-one compounds.

Preferred fluorinating agents are aminofluorosulfuranes in which, in formula (III), $R^5$ and $R^6$ are $C_1$- to $C_3$-alkyl, or $R^5$ and $R^6$ together are the —$(CH_2)_2$—O—$(CH_2)_2$— group (see, for example, M. Hudlicky in Org. Reactions 53, 513). Diethylaminosulfur trifluoride and morpholinosulfur trifluoride are particularly preferably employed.

The invention is illustrated in more detail by the following examples:

Example 1

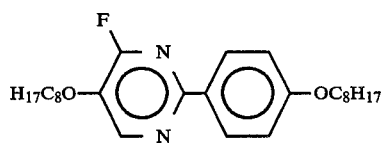

4-Fluoro-5-octyloxy-2-(4-octyloxyphenyl)pyrimidine
Preparation:
A solution of 0.7 ml of diethylaminosulfurtrifluoride (DAST) in 10 ml of dichloromethane is added in the course of 10 minutes, at 0° C., to a suspension of 2.1 g of 5-octyloxy-2-(4-octyloxyphenyl)pyrimidin-4-one (prepared, for example, in accordance with Boller et al., Z. Naturf. 33b, 433 (1978)) in 30 ml of dichloromethane. After 8 h at 40° C., aqueous sodium bicarbonate solution is added. After chromatography and recrystallization from acetonitrile, the organic phase yields 0.7 g of colorless crystals.
Phase sequence X 43.5 $S_c$ 52 N 64.2 I
Comparison Example 1b
The non-fluorinated comparison compound has a melting point of 51° C., which is 7° C. higher.
The following are obtained analogously:

Example 2

4-Fluoro-5-heptyl-2-(4-octyloxyphenyl)pyrimidine
Phase sequence X 40 N 43.8 I

Example 3

4-Fluoro-5-octyl-2- (4-octyloxyphenyl)pyrimidine
Phase sequence X 37 N 41.5 I

Example 4

4-Fluoro-5-nonyl-2-(4-octyloxyphenyl)pyrimidine
Phase sequence X 34 N 45 I

Example 5

5-Decyl-4-fluoro-2-(4-octyloxyphenyl)pyrimidine
Phase sequence X 36 N 43 I

Example 6

2-(4-Ethoxyphenyl)-4-fluoro-5-octyloxypyrimidine
Phase sequence X 70.5 (N) 55 I

Example 7

5-[4-(Butyldimethylsilyl)butyloxy]-4-fluoro-2-(4-octyloxyphenyl)pyrimidine
Phase sequence X 12.4 N 16 I

Example 8

4-Fluoro-5-octyloxy-2-[4-(4-trans-pentylcyclohexyl)-phenyl]pyrimidine
Phase sequence X 71 ($S_c$) 61 N 148 I

Comparison Example 8b

Up to 83° C. the non-fluorinated comparison substance has a more highly ordered smectic phase. Apparently the fluorine substitution leads to a suppression of the more highly ordered smectic phase and thus to an extension of the $S_c$ phase to low temperatures.

Example 9

2-[4-(4-Cyclopropylbutyloxy)phenyl]-4-fluoro-5-octyloxypyrimidine
Phase sequence X (45 N) 62 I

Example 10

2-[4-(8-Cyclopropyloctyloxy)phenyl]-4-fluoro-5-octyloxypyrimidine
Phase sequence X 51 ($S_c$ 45 N 55) I

Example 11

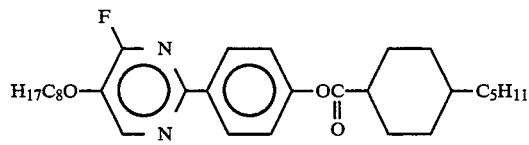

4-Fluoro-5-octyloxy-2-[4-(4-trans-pentylcyclohexylcarbonyloxy)phenyl]pyrimidine
Preparation:
0.45 ml of diethylaminosulfur trifluoride is added to a solution of 1.6 g of 5-octyloxy-2-[4-(4-trans-pentylcyclohexylcarbonyloxy)phenyl]pyrimidine-4-one (obtained by reaction of 2-(4-hydroxyphenyl)-5-octyloxypyrimidin-4one —preparation in accordance with Boller et al.—with trans-4-pentylcyclohexanecarboxylic acid by means of dicyclohexylcarbodiimide) in 40 ml of dichloromethane and the mixture is kept at 20° C. for 16 h. After working up as in Example 1 and recrystallization from n-hexane, 0.3 g of colorless crystals are obtained. Phase sequence X 80 $S_c$ 87 N 173 I This $S_c$ phase is existent up to crystallization at 60° C.

Comparison Example 11b

The non-fluorinated comparison substance, on the other hand, has a more highly ordered smectic phase at 74° C., which phase is apparently suppressed by the fluorination.
The following are obtained analogously:

Example 12

4-Fluoro-5-octyl-2-[4-(4-trans-pentylcyclohexylcarbonyloxy)phenyl]pyrimidine

Phase sequence X 78 N 137 I

Example 13

4-(4-Fluoro-5-octyloxypyrimidin-2-yl)phenyl (2R, 3R)-3-propyloxiranecarboxylate

Optical rotation $[\alpha]_D^{20} = -24.9°$ (c=2, 1,2-dichloroethane)

Phase sequence X 90 I

Example 14

2-(Octyloxyphenyl)-4-fluoro-5-(4'-trans-pentylcyclohexylcarbonyloxy)pyrimidine

Phase sequence X 61 $S_c$ 77 N 188 I

Comparison Example 14b

2-Dodecyloxyphenyl-5-(4'-trans-pentylcyclohexanecarbonyloxy)pyrimidine

Phase sequence X 90 $S_A$ 185 N 188

The substance according to the invention has a low melting point and instead of the $S_A$ phase a $S_c$ phase is observed. The fluorine substitution leads to a suppression of the orthogonal $S_A$ phase and to an intensification of the tilted $S_c$ phase.

Example 15

Ethyl 4-fluoro-2-(4-trans-pentylcyclohexyl)-pyrimidine-5-carboxylate

X 37 I

Example 16

4-Octyloxyphenyl 4-fluoro-2-(4-trans-pentylcyclohexyl)-pyrimidine-5-carboxylate

X 80 $S_c$ 98 $S_A$ 118 N 143 I

Example 17

4-(5-Octylpyrimidin-2-yl)phenyl 4-fluoro-2-(4-transpentylcyclohexyl)pyrimidine-5-carboxylate

X 120 N 233 I

Use Example 1

A ferroelectric mixture consists of the following components

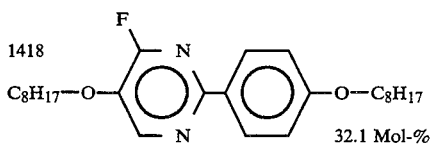

1418   32.1 Mol.-%

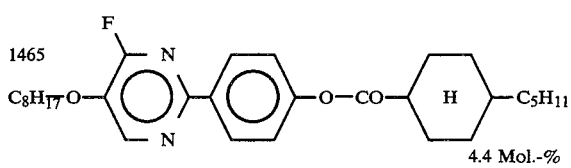

1465   4.4 Mol.-%

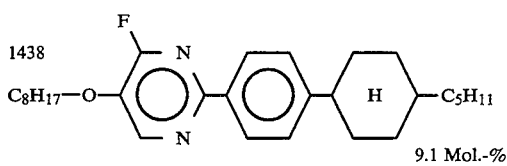

1438   9.1 Mol.-%

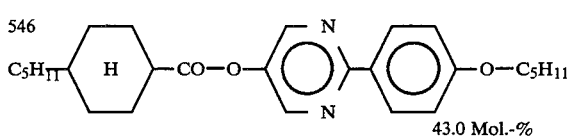

546   43.0 Mol.-%

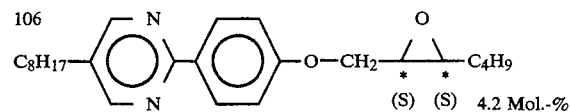

106   (S) (S)   4.2 Mol.-%

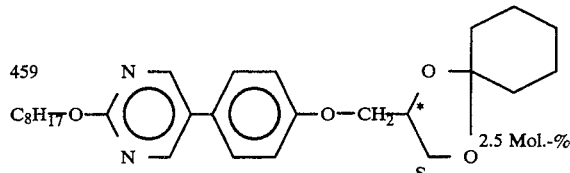

459   2.5 Mol.-%

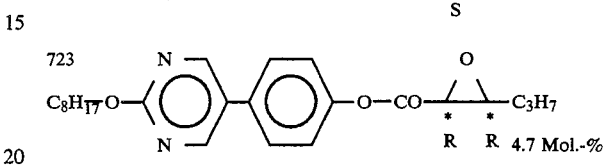

723   R R   4.7 Mol.-% and has the following phase sequence $S_c^*$ 84 $S_A^*$ 97 N* 125 I

This mixture switches at a temperature of 60° C. at a field strength of 10 V $\mu m^{-1}$ in a 2 $\mu m$ thick cell with a response time of 140 $\mu sec$.

Use Example 2

A mixture consisting of the components

| | |
|---|---|
| 5-Octyloxy-2-(4-hexyloxyphenyl)pyrimidine | 8.6 Mol-% |
| 5-Octyloxy-2-(4-butyloxyphenyl)pyrimidine | 9.0 Mol-% |
| 5-Octyloxy-2-(4-decyloxyphenyl)pyrimidine | 7.2 Mol-% |
| 5-Octyloxy-2-(4-octyloxyphenyl)pyrimidine | 4.0 Mol-% |
| 5-Octyl-2-(4-hexyloxyphenyl)pyrimidine | 13.7 Mol-% |
| 5-Octyl-2-(4-octyloxyphenyl)pyrimidine | 12.3 Mol-% |
| 5-Octyl-2-(4-decyloxyphenyl)pyrimidine | 9.2 Mol-% |
| 4'-(5-Dodecylpyrimidin-2-yl)phenyl trans-4-pentylcyclohexanecarboxylate | 13.6 Mol-% |
| 4-Fluoro-5-octyloxy-2-(4-octyloxyphenyl)-pyrimidine | 4.9 Mol-% |
| (2S,3S)-2-(4-Octylpyrimidin-2-yl)phenyloxy)-methyl-3-butyloxirane | 5.7 Mol-% |
| 4-(2-Octyloxypyrimidin-5-yl)phenyl (2R,3R)-3-propyloxirane-2-carboxylate | 6.4 Mol-% |
| (S)-4-(2-Octyloxypyrimidin-5-yl)phenyl spiro-(1,3-dioxolane-2,1-cyclohexan-4-yl)-methyl ether | 3.4 Mol-% |
| 4,7,13,16,21,24-Hexaoxa-1,10-diazabicyclo-[8.8.8.]hexacosane | 1.0 Mol-% |
| 2,5,8,15,18,21-Hexaoxatricyclo[20.4.0.0]-hexacosane | 1.0 Mol-% | shows the following liquid crystal phase regions:

$S_c$ 58 $S_A$ 62 N 80 I and at 25° C. has a spontaneous polarization of 27.5 nC/cm.

In a 2 $\mu m$ thick polyimide-coated cell at an applied pulse field strength of 10 V$\mu m^{-1}$, the ferroelectric mixture switches with a pulse width of 114 $\mu s$.

This example confirms that fast-switching ferroelectric mixtures can be prepared using the compounds according to the invention.

Use Example 3 a) A mixture consisting of the components

| | |
|---|---|
| 5-Octyloxy-2-(4-hexyloxyphenyl)pyrimidine | 8.6 Mol-% |
| 5-Octyloxy-2-(4-butyloxyphenyl)pyrimidine | 9.0 Mol-% |
| 5-Octyloxy-2-(4-decyloxyphenyl)pyrimidine | 7.2 Mol-% |
| 5-Octyloxy-2-(4-octyloxyphenyl)pyrimidine | 4.0 Mol-% |

| | |
|---|---|
| 5-Octyl-2-(4-hexyloxyphenyl)pyrimidine | 13.7 Mol-% |
| 5-Octyl-2-(4-octyloxyphenyl)pyrimidine | 12.3 Mol-% |
| 5-Octyl-2-(4-decyloxyphenyl)pyrimidine | 9.2 Mol-% |
| 4'-(5-Dodecylpyrimidin-2-yl)phenyl trans-4-pentylcyclohexanecarboxylate | 13.6 Mol-% |
| 4-Fluoro-5-octyloxy-2-(4-octyloxyphenyl)-pyrimidine | 4.9 Mol-% |
| (2S,3S)-2-(4-Octylpyrimidin-2-yl)phenyloxy)-methyl-3-butyloxirane | 5.7 Mol-% |
| 4-(2-Octyloxypyrimidin-5-yl)phenyl (2R,3R)-3-propyloxirane-2-carboxylate | 6.4 Mol-% |
| (S)-4-(2-Octyloxypyrimidin-5-yl)phenyl spiro-(1,3-dioxolane-2,1-cyclohexan-4-yl)-methyl ether | 3.4 Mol-% |
| 4,7,13,16,21,24-Hexaoxa-1,10-diazabicyclo[8.8.8.]hexacosane | 1.0 Mol-% |
| 2,5,8,15,18,21-Hexaoxatricyclo[20.4.0.0]-hexacosane | 1.0 Mol-% | shows the following liquid crystal phase regions:
X −4 S$_c$ 57 S$_A$ 63 N 82 I
and at 25° C. has a spontaneous polarization of 27 nC/cm. In a 2 μm thick polyimide-coated cell at an applied pulse field strength of 10 Vμm$^{-1}$, the ferroelectric mixture switches with a pulse width of 93 μs.

b) A comparison mixture which differs from the above-mentioned mixture only in that it contains no fluoropyrimidine component, has a spontaneous polarization of 27 nC/cm at 25° C. and shows the following liquid crystal phase regions:
X −4 S$_c$ 57 S$_A$ 68 N 83 I In a 2 μm thick polyimide-coated cell at an applied pulse field strength of 10 Vμm$^{-1}$, the ferroelectric mixture switches with a pulse width of 115 μs. This example shows that the compounds according to the invention contribute to a shortening of the response time in ferroelectric mixtures. Moreover, the mixture containing the component according to the invention has a broader phase.

We claim:

1. A ferroelectric liquid crystal mixture comprising 2 to 20 components and comprising at least one 4-fluoropyrimidine of the formula (I):

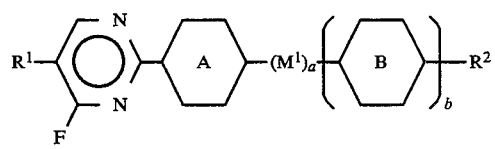

(I)

in which the symbols have the following meaning:
R$^1$ and R$^2$ independently of one another are straight-chain or branched alkyl having 1 to 16 carbon atoms, it being possible for one or two non-adjacent —CH$_2$— groups to be replaced by —O—, —S—, —CO—, —CO—O—, —O—CO—, —CH=CH—, —OC(O)O—, —C≡C—,

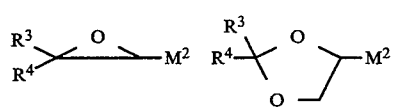

or —Si(CH$_3$)$_2$—, or are one of the following groups:

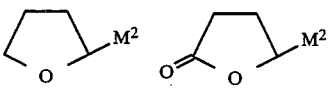

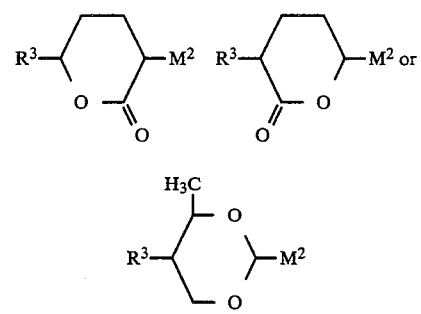

R$^3$ and R$^4$ independently of one another are H or alkyl having 1 to 16 carbon atoms or alkenyl having 2 to 16 carbon atoms, or R$^3$ and R$^4$ together are —(CH$_2$)$_4$— or —(CH$_2$)$_5$—, —M$^1$— is —CO—O, —O—CO—, —CH$_2$—O—, —O—CH$_2$—, —C≡C—, —CH=CH—, —CH$_2$—CH$_2$—, —CH$_2$CH$_2$CH$_2$CH$_2$—, —CH$_2$CH$_2$CH$_2$O—

—M$^2$— is CH$_2$—O—, —O—CH$_2$, $$-\overset{\overset{O}{\|}}{C}O-, -O-\overset{\overset{O}{\|}}{C}-,$$

or a single bond
a and b independently of one another are zero or one, on condition that a is zero if b is zero, and

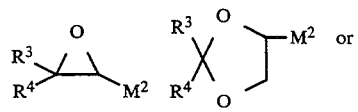

independently of one another are 1,4-phenylene, 1,4-cyclohexylene, 2,5-pyridinediyl or (1,3,4)thiadiazol-2,5-diyl.

2. A mixture as claimed in claim 1, wherein the symbols in formula (I) have the following meaning:
R$^1$ and R$^2$ independently of one another are alkyl having 1 to 16 carbon atoms, it being possible for the —CH$_2$— group to be replaced by —O—, —CO—O—, —O—CO—, or —Si(CH$_3$)$_2$—, or are -continued

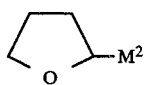

—M¹— is —CO—O, O—CH—, CH₂O or —OCH₂—
—M²— is —CO—O— or —CH₂O—

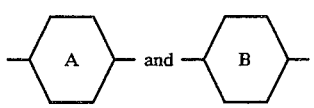

independently of one another are 1,4-phenylene or 1,4-cyclohexylene,
R³ and R⁴ are both H or C₁-C₅-alkyl, or R³ and R⁴ together are —(CH₂)₅—, and
a, b independently of one another are zero or one, on condition that a is zero if b is zero.

3. A mixture as claimed in claim 1, wherein the symbols in formula (I) have the following meaning:
R¹ and R² independently of one another are alkyl having 5 to 12 carbon atoms, it being possible for one —CH₂— group to be replaced by —O— and for a further —CH₂— group to be replaced by

or are

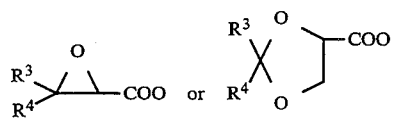

—M¹— is —CO—O— or —O—CO—,

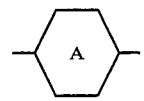

is 1,4-phenylene,

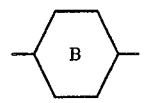

is 1,4-cyclohexylene and
R³ and R⁴ are both H or C₁-C₅-alkyl, or R³ and R⁴ together are —(CH₂)₅—, and
a=b and is zero or one.

4. A mixture as claimed in claim 1, wherein, in formula (I), the groups R¹ and R² independently of one another are alkyl having 5 to 12 carbon atoms, it being possible for one —CH₂— group to be replaced by —CO—O—, —O—CO— or —O— and the terminal —CH₂— group being replaced by

5. A ferroelectric liquid crystal switching and display element comprising support plates, electrodes, at least one orientation layer, and a ferroelectric liquid crystal medium, which element contains a ferroelectric liquid crystal mixture as claimed in claim 1 as liquid crystal medium.

6. A ferroelectric liquid crystal switching and display element as claimed in claim 5, further comprising an antireflex, passivation, compensation or barrier layer.

7. A mixture as claimed in claim 1, wherein the compound of the formula (I) is 4-fluoro-5-octyl-oxy-2-(4-octyloxyphenyl) pyrimidine.

* * * * *